United States Patent
Liu et al.

(10) Patent No.: US 9,993,510 B2
(45) Date of Patent: *Jun. 12, 2018

(54) ACNE-REMOVING TRADITIONAL CHINESE MEDICINE COMPOSITION AND PREPARATION METHOD THEREOF

(71) Applicant: INFINITUS (CHINA) COMPANY LTD, Jiangmen, Guangdong (CN)

(72) Inventors: Guangrong Liu, Guangdong (CN); Wenjuan Deng, Guangdong (CN); Jian Tang, Guangdong (CN)

(73) Assignee: INFINITUS (CHINA) COMPANY LTD, Jiangmen, Guangdong (CN)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/538,104

(22) PCT Filed: Jun. 24, 2016

(86) PCT No.: PCT/CN2016/087101
§ 371 (c)(1),
(2) Date: Jun. 20, 2017

(87) PCT Pub. No.: WO2017/036241
PCT Pub. Date: Mar. 9, 2017

(65) Prior Publication Data
US 2017/0348372 A1    Dec. 7, 2017

(30) Foreign Application Priority Data
Aug. 28, 2015  (CN) .......................... 2015 1 0540785

(51) Int. Cl.
*A61K 36/752* (2006.01)
*A61K 36/53* (2006.01)
*A61K 8/96* (2006.01)
*A61Q 19/00* (2006.01)

(52) U.S. Cl.
CPC .............. *A61K 36/752* (2013.01); *A61K 8/96* (2013.01); *A61K 36/53* (2013.01); *A61Q 19/00* (2013.01)

(58) Field of Classification Search
None
See application file for complete search history.

(56) References Cited

U.S. PATENT DOCUMENTS 6,136,329 A    10/2000   Boratyn

FOREIGN PATENT DOCUMENTS

| CN | 105168478 A | 12/2015 |
|----|-------------|---------|
| CN | 105168479 A | 12/2015 |
| JP | 2003231607 A | 8/2003 |
| JP | 2004161623 A | 6/2004 |
| JP | 2005200339 A | 7/2005 |
| WO | 2017036239 A1 | 3/2017 |

OTHER PUBLICATIONS

U.S. Appl. No. 15/540,479, filed Jun. 2017, Deng, Wenjuan.*
Pothitirat, W., et al., Fitoterapia, 80:442. (Year: 2009).*
Mullaicharam, et al., J. Biomed. Pharm. Res., 3:28. (Year: 2012).*
Mohamed, et al., Energy Conversion and Management 46:1473. (Year: 2005).*
International Search Report for PCT/CN2016/087101, dated Aug. 19, 2016, ISA/CN.
Wang Yuan, "King" and "Queen" of Tropical fruit, Encyclopedic Knowledge, No. 5 p. 43.
Liu Jixin et al., Observation on the inhibitory effect of fructus aurantii on human demodex in vitro, Chinese Journal of Zoonoses, No. 5, vol. 24, p. 485.
Wang Suling et al., Development and utilization of wild thyme in Heilongjiang province, Special Economic Animal and Plant, No. 12 p. 25.
The Japanese 1st Office Action for JP2017-537360 dated Apr. 3, 2018 along with its English Brief Summary.

* cited by examiner

*Primary Examiner* — Michael Barker
(74) *Attorney, Agent, or Firm* — U.S. Fairsky LLP; Yue Xu

(57) ABSTRACT

Disclosed are an acne-removing traditional Chinese medicine composition and a preparation method thereof, wherein the traditional Chinese medicine composition is made from *Garcinia mangostana* L pericarp, thyme and *Fructus aurantii* through steps of ethanol extraction and macroporous resin, and collecting the part eluted by 60%-80% ethanol. The three medicinal materials of the composition have a synergic anti-inflammation effect.

10 Claims, No Drawings

ACNE-REMOVING TRADITIONAL CHINESE MEDICINE COMPOSITION AND PREPARATION METHOD THEREOF

The present disclosure is the national phase of International Application No. PCT/CN2016/087101, titled "ACNE-REMOVING TRADITIONAL CHINESE MEDICINE COMPOSITION AND PREPARATION METHOD THEREOF", filed on Jun. 24, 2016, which claims the priority to Chinese Patent Application No. 201510540785.6 titled "ACNE-REMOVING TRADITIONAL CHINESE MEDICINE COMPOSITION AND PREPARATION METHOD THEREOF", filed on Aug. 28, 2015 with the State Intellectual Property Office of the People's Republic of China, which is incorporated herein by reference in entirety.

FIELD

The present invention relates to the field of traditional Chinese medicine, and in particular to an acne-removing Chinese medicine composition and preparation method thereof.

BACKGROUND

Acne (also known as whelk, acne vulgaris, pimple), is a common skin disease which can cause inflammation of human skin sebaceous glands or hair follicles. Spine-shape papules, from which white or creamy white broken rice like juice can be squeezed out, are formed in local lesions. The development of acne is mainly related to the factors, such as excessive sebum secretion, the duct clog of folliculosebaceous, bacteria infections and inflammation reactions. After people enter into their adolescence, the level of androgen, especially testosterone, is increased rapidly, promoting development of sebaceous glands and a large secretion of sebum. At the meantime, the abnormal follicular keratosis of the sebaceous gland ducts causes the clog of ducts, dyssebacia and the formation of keratotic plug (i.e. micro-acne). Various microbes, especially *Propionibacterium acnes*, overgrow in hair follicle. The lipases generated by *Propionibacterium acnes* degrade the sebum into free fatty acids, promote the chemotaxis of inflammatory cells and mediators, and finally induce and aggravate inflammation.

Acne often occurs in young people, in both sexes. It is more commonly found in male than in female, but the age of onset in female is earlier than in male. Acne occurs mostly in face, forehead, cheek and nasolabial fold, next in chest, back and shoulder. Usually, the skin damage caused by acne does not have subjective symptom. Pain may be accompanied under severe inflammation reactions. Acne can be classified into acne, papule, pustule and nodular cyst. Acne affects 80-90% of teenagers. After adolescence, acnes often can be abated automatically or cured, except that acne persists in some patients into their thirties. Although acne has a tendency of self-healing, the acnes themselves and scars caused by the acnes without timely treatment may severely affect the life quality of patient and cause mental pressure and financial burden of patients. Attentions should be paid to these problems.

There are six common treatment methods of acne, including:
(1) Drugs for local and external application: tretinoin (tretinoin cream, adapalene gel, tazarotene gel), benzoyl peroxide, antibiotics (clindamycin, erythromycin, chloramphenicol, etc.), azelaic acid, sulfur lotion, etc.;
(2) Oral antibiotics: the first choice is tetracyclines (minocycline, doxycycline, etc.); secondary choice is macrolides (erythromycin); antibiotics which are used for systemic infection treatment, such as levofloxacin, should be avoided. The duration of antibiotic treatment is usually 6-12 weeks.
(3) Oral isotretinoin: for severe acne, oral isotretinoin is the standard treatment and also the most effective treatment so far. The course treatment endpoint is the minimal accumulated dose of 60 mg/kg.
(4) Antiandrogen treatment: for example, oral contraceptive compound cyproterone acetate tablets (trade name: Diane-35), is suitable for female patients of moderate and severe acne. For female patients who have symptoms of high level of androgen (such as hirsutism, seborrhoeia, etc.), polycystic ovary syndrome, late-onset acne and those whose acne becomes intense before their menstrual period, oral contraceptives can also be taken into consideration.
(5) Oral glucocorticoid: it is mainly used for fulminant acne or acne conglobata. The treatments follow the principle of short term, small dose and combination with other treatments.
(6) Others: for the patient who is intolerant to the drug or unwilling to accept drug treatment, physical therapy can also be considered, such as photodynamic therapy (PDT), fruit acid therapy, laser therapy, etc.

The acne treatments should be divided into different stages: stage 1, usually local treatment is adopted and external administration of tretinoins are preferred; stage 2, the combinations of external administration of tretinoins and benzoyl peroxide or antibiotics are used, and oral antibiotics are combined if needed; stage 3, usually combination treatments are needed and the combinations of oral antibiotics with external use benzoyl peroxide and/or tretinoins are first choice; for female patients with indications, antiandrogen treatment may also be taken into consideration. Stage 4, oral isotretinoin is the most effective treatment and can be used as a first-line therapy. For the patients who have inflammatory papules and more pustules, the combination of antibiotic and external benzoyl peroxide can also be applied systemically. After the skin damage is improved obviously, the oral isotretinoin is then applied for sequential treatment.

However, at present, western medicines occupy the main portion of the drug market for acne treatment. Although the western medicines can achieve the effect of acne removing, they have relatively obvious side-effects. So they are not suitable for long-term use and the dose thereof should not be too high. For people from adolescent to adult phase who have frequent and repeating acne occurrences, the acne-removing products which are natural and gentle, with less side-effects and suitable for long-term use are needed.

SUMMARY

In view of the above, the object of the present invention is to provide an acne-removing Chinese medicine composition and preparation method thereof. The Chinese medicine composition described herein has a dramatic effect on acne treatment and a high cure rate, which is natural, gentle and suitable for long-term use.

To achieve the object of the present invention, the following technical solution is adopted in the present invention:

An acne-removing Chinese medicine composition is provided, which is made from the following raw materials (parts by weight):

| | |
|---|---|
| mangosteen (*Garcinia mangostana* L.) pericarp | 60 to 80 parts |
| thyme (*Thymus mongolicus* R.) | 10 to 20 parts |
| fructus aurantii | 10 to 20 parts. |

The Chinese medicine composition of the present invention is made from mangosteen pericarp, thyme and *fructus aurantii*. These medicines in the Chinese medicine composition affect each other and have a synergic effect on anti-bacteria and anti-inflammation.

Herein, the scientific name of mangosteen is *Garcinia mangostana* L. The nature of mangosteen is warm and its taste is sweet and sour. It can tonify the spleen, promote the salivary secretion and stop diarrhea. The property of mangosteen pericarp is cool in nature and is bitter in taste, which has effects on anti-inflammation and pain relieving.

Thyme is also called *thymus vulgaris*, *Thymus mongolicus* R., including thyme or Mongollian Thyme Herb (*Thymus przewalskii*), belonging to *Thymus* genus, Labiatae family. The whole plant is used as a medicine. To prepare the raw material, thyme is collected in summer when it is rich in leaves and branches. After the whole plant is cleaned and the root is removed (can be used for reproduction), it is cut into pieces and used freshly or after it is dried. The nature of thyme is slightly warm and it tastes spicy. It has the functions of dispelling wind to relieve exogenous syndrome, promoting qi circulation to relieve pain, stopping cough and reducing blood pressure. It is mainly used in the treatments of cold, cough, headache, toothache, dyspepsia, acute gastroenteritis and high blood pressure.

*Fructus aurantii* is the dried immature fruit of *Citrus aurantium* L. and its cultivated varieties. *Fructus aurantii* is harvested in July when the peel is still green, it is cut in half from the middle, dried in the air or at a low temperature. *Fructus aurantii* is bitter, spicy, sour and warm in nature. It has the functions of regulating qi and loosening center, activating stagnancy and relieving distension. It is mainly used in the treatments of Qi stagnation in chest and rib, swelling or pain, indigestion of food retention, congestion of fluid-retention, gastroptosis, archoptosis, uterine prolapse, and the like.

Mangosteen pericarp, thyme and *Fructus aurantii* described in the present invention are well-known to those of ordinary skill in the art and commercially available by purchasing from the drugstores; or they can be cultured and collected through the method disclosed in the prior art, as long as they meet the national or industry standards.

A preparation method of the acne-removing Chinese medicine composition is also provided in the present invention, comprising: mixing 60 to 80 by weight parts of mangosteen pericarp, 10 to 20 by weight parts of thyme and 10 to 20 by weight parts of *Fructus aurantii*; extracting with ethanol; collecting and purifying the extraction solution.

According to the present invention, in some embodiments, in the preparation method of the present invention, the ethanol extraction is performed by using 8 to 12 folds (by weight) of 76%-95% of ethanol-water solution for heating reflux extraction for 1 h-2.5 h.

According to the present invention, in some embodiments, the purification method described in the preparation method of the present invention, comprises steps of:
  a. extraction solution is concentrated after filtration; the concentrated extract is dissolved in ethanol-water solution and refrigerated overnight; and
  b. filtration is performed, the filtrate is adsorbed by macroporous adsorption resin and eluted by elution solution.

Herein, in some embodiments, in step a, the concentration is preferably conducted to a specific gravity of 1.05 to 1.1.

In some embodiments, in step a, the volume ratio of ethanol in the ethanol-water solution is 70%-80%.

Further, in some embodiments, the amount of ethanol-water solution used in step a is 4 to 6 folds by weight of that of the concentrated solution.

In some embodiments, in step a, the temperature for dissolving the concentrated solution in ethanol-water solution is 50° C. to 80° C.; and the dissolving duration is 0.5 h-2 h.

In some embodiments, in step a, the refrigeration overnight is performed by placing at 0° C. to 4° C. for 12 h-18 h.

According to the present invention, in some embodiments, in the preparation method of the present invention, in step b the elution is performed by eluting with water, 20%-40% ethanol-water solution, 60%-80% ethanol-water solution, successively, and the fragment eluted by 60%-80% ethanol-water solution is collected.

Herein, the amount of water used is 1BV-2BV, the amount of 20%-40% ethanol-water solution used is 1BV-2BV and the amount of 60%-80% ethanol used is 2BV-4BV.

In some embodiments, in step b, the elution is performed by eluting with water, 40% ethanol-water solution, 80% ethanol-water solution, and the fragment eluted by 80% ethanol-water solution is collected.

According to the present invention, in some embodiments, in the preparation method of the present invention, the fragment eluted by 60%-80% ethanol-water solution in step b is concentrated and dried. In some embodiments, the fragment is concentrated to a specific gravity of 1.05 to 1.1 and then spray drying is performed.

In some embodiments, in step b a further step of concentrating the solution after filtration is still comprised. It is preferred that the concentration step is conducted to a specific gravity of 1.05 to 1.1.

As appreciated by a person skilled in the art, the concentration in the preparation method of the present invention can be conducted by any known method in the art. In some specific examples, the concentration mentioned in the preparation method of the present invention is preferably reduced pressure concentration. The specific conditions are temperature of 60° C.-80° C., and vacuum degree ≥0.08 Mpa.

A Chinese medicine composition prepared is also provided in the present invention.

Preparations containing the Chinese medicine composition are also provided in the present invention. The preparations described here can be medicaments or cosmetics. Herein the medicaments can be an external preparation that is well known in the field, such as liniment, ointment, cream, paste, film, coating, gel, aerosol, spray, patch, etc. Herein the cosmetics can be the well-known types, such as facial cream, emulsion, essence, facial mask, eye cream, basal solution, etc.

According to different needs of a user, a person skilled in the art can prepare the Chinese medicine composition of the present invention into different dosage forms by adding various common excipients needed. The common preparations described here can be prepared through common formulation methods and processes.

Preferably, the preparation of the Chinese medicine composition in the present invention is ointment and cream. They have the advantages of easy use, strong pertinence and remarkable therapy effect.

The dose and regimen for the pharmaceutical composition and its preparations depend on many factors, including age, weight, sex, health status and nutrition status of the user, activity intensity of the compound, duration, metabolic rate, severity of the disease and the judgment of the doctor. A person skilled in the art can easily decide the dose and regime of the pharmaceutical composition according to the factors described above.

The present invention provides an acne-removing Chinese medicine composition and a preparation method thereof. The Chinese medicine composition of the present invention is made from mangosteen pericarp, thyme and *Fructus aurantii* as raw materials. Through the anti-inflammation efficacy test in mouse dermatitis model and *Propionibacterium acnes* bacteriostasis test, it was demonstrated that the Chinese medicine composition of the present invention has excellent effects on the inhibition of *Propionibacterium acnes* and anti-inflammation efficacy. These three medicinal materials have a synergic effect on anti-inflammation. They work rapidly and have an excellent effect. The Chinese medicine composition of the present invention are made from natural raw materials, and does not contain pigments, preservatives, and any other auxiliary and functional additives. The Chinese medicine composition is safe and mild, and has no irritation and side-effect and can be used for a long time, which is widely suitable for the teenagers and the adults who are bothered by acne for a long time. The preparation method of the Chinese medicine composition of the present invention uses only ethanol-water solution in extraction and dissolving steps, without need of using toxic organic solvents. The solvent used in the process of the preparation method can also be recycled and reused, which reduces the cost and protects the environment. The instruments used in the preparation method of the Chinese medicine composition of the present invention are common instruments in Chinese medicine manufacture, including the instruments for reflux extraction, filtration, reduced pressure concentration, resin adsorption and elution, and spay drying. The process steps are easy to be handled, and the yield of product and active ingredients is high, thus the method is suitable for industrialized production.

DETAILED DESCRIPTION OF EMBODIMENTS

Hereinafter, the technical solutions in the examples of the present invention will be described clearly and completely in conjunction with examples of the present invention. It is apparent that the described examples are merely a part of the examples of the present invention rather than all.

Based on the examples of the present invention, all other examples obtained by a person skilled in the art without creative work are within the scope of the present invention.

To further understand the present invention, detailed descriptions are provided in combination with the following examples.

Example 1: An Acne-Removing Chinese Medicine Composition of the Present Invention 1. Mangosteen pericarp, thyme and *Fructus aurantii* were crushed respectively, passed through a 60-mesh sieve, and mixed in a ratio of 80 g mangosteen pericarp, 20 g thyme and 20 g *Fructus aurantii*;
2. reflux extraction was performed for 2.5 h by using 95% ethanol-water solution in a amount of 12 folds by weight of the raw materials;
3. the above extraction solution was filtered through 100-mesh filter cloth to remove the residue, concentrated under reduced pressure (temperature 60° C.-80° C., vacuum degree ≥0.08 Mpa, the same below) to obtain 72 g concentrated solution with a specific gravity of 1.08;
4. recycled ethanol-water solution was adjusted to a concentration of 80%, added to the concentrated solution at a volume ratio of 6:1 (ethanol-water solution:concentrated solution); stirred and dissolved at 80° C. for 2 h, and refrigerated overnight at 4° C. for 18 h;
5. the refrigerated solution was filtered and the filtrate was concentrated under reduced pressure to obtain 40 g product with a specific gravity of 1.08;
6. the concentrated solution was adsorbed by polyamide resins and eluted with water, 40% ethanol-water solution, 80% ethanol-water solution respectively, wherein the amount of water used is 1BV, the amount of 40% ethanol-water solution used is 1BV, and the amount of 80% ethanol-water solution used is 4BV;
7. a fragment eluted by 80% ethanol-water solution was collected and concentrated under reduced pressure to a specific gravity of 1.06, followed by spay drying to obtain 5.04 g.

Example 2: An Acne-Removing Chinese Medicine Composition of the Present Invention 1. Mangosteen pericarp, thyme and *Fructus aurantii* were crushed respectively, passed through a 60-mesh sieve, and mixed in a ratio of 60 g mangosteen pericarp, 10 g thyme and 10 g *Fructus aurantii*;
2. reflux extraction was performed for 1 h by using 60% ethanol-water solution in an amount of 8 folds by weight of the raw materials;
3. the above extract was filtered through 100-mesh filter cloth to remove the residue, concentrated under reduced pressure (temperature 60° C.-80° C., vacuum degree ≥0.08 Mpa, the same below) to obtain 106 g concentrated solution with a specific gravity of 1.08;
4. recycled ethanol-water solution was adjusted to a concentration of 60%, added to the concentrated solution at a volume ratio of 4:1 (ethanol-water solution:concentrated solution); stirred and dissolved at 50° C. for 0.5 h, and refrigerated overnight at 0° C. for 12 h;
5. the refrigerated solution was filtered and the filtrate was concentrated under reduced pressure to obtain 76 g product with a specific gravity of 1.08;
6. the concentrated solution was adsorbed by polyamide resins and eluted with water, 40% ethanol-water solution, 80% ethanol-water solution respectively, wherein the amount of water used is 2BV, the amount of 40% ethanol-water solution used is 2BV, and the amount of 80% ethanol-water solution used is 2BV;
7. a fragment eluted by 80% ethanol-water solution was collected and concentrated under reduced pressure to a specific gravity of 1.06, followed by spay drying to obtain 3.2 g.

Example 3: An Acne-Removing Chinese Medicine Composition of the Present Invention 1. Mangosteen pericarp, thyme and *Fructus aurantii* were crushed respectively, passed through a 60-mesh sieve, and mixed in a ratio of 80 g mangosteen pericarp, 10 g thyme and 10 g *Fructus aurantii*;
2. reflux extraction was performed for 2 h by using 75% ethanol-water solution in a amount of 10 folds by weight of the raw materials;

3. the above extract was filtered through 100-mesh filter cloth to remove the residue, concentrated under reduced pressure (temperature 60° C.-80° C., vacuum degree ≥0.08 Mpa, the same below) to obtain 106 g concentrated solution with a specific gravity of 1.06;

4. recycled ethanol-water solution was adjusted to a concentration of 70%, added to the concentrated solution at a volume ratio of 5:1 (ethanol-water solution:concentrated solution); stirred and dissolved at 60° C. for 1 h, and refrigerated overnight at 2° C. for 15 h;

5. the refrigerated solution was filtered and the filtrate was concentrated under reduced pressure to obtain 76 g product with a specific gravity of 1.08;

6. the concentrated solution was adsorbed by polyamide resins and eluted with water, 40% ethanol-water solution, 80% ethanol-water solution respectively, wherein the amount of water used is 1BV, the amount of 40% ethanol-water solution used is 2BV, and the amount of 80% ethanol-water solution used is 3BV;

7. a fragment eluted by 80% ethanol-water solution was collected and concentrated under reduced pressure to a specific gravity of 1.06, followed by spay drying to obtain 4.4 g.

Comparative Example 1

1. 100 g Mangosteen pericarp was crushed, and passed through a 60-mesh sieve;

2. reflux extraction was performed for 2 h by using 75% ethanol-water solution in a amount of 10 folds by weight of the raw materials;

3. the above extract was filtered through 100-mesh filter cloth to remove the residue, concentrated under reduced pressure (temperature 60° C.-80° C., vacuum degree ≥0.08 Mpa, the same below) to obtain 62 g concentrated solution with a specific gravity of 1.06;

4. recycled ethanol-water solution was adjusted to a concentration of 70%, added to the concentrated solution at a volume ratio of 5:1 (ethanol-water solution:concentrated solution); stirred and dissolved at 60° C. for 1.5 h, and refrigerated overnight at 2° C. for 15 h;

5. the refrigerated solution was filtered and the filtrate was concentrated under reduced pressure to obtain 54 g product with a specific gravity of 1.08;

6. the concentrated solution was adsorbed by polyamide resins and eluted with water, 40% ethanol-water solution, 80% ethanol-water solution respectively, wherein the amount of water used is 1BV, the amount of 40% ethanol-water solution used is 2BV, and the amount of 80% ethanol-water solution used is 3BV;

7. a fragment eluted by 80% ethanol-water solution was collected and concentrated under reduced pressure to a specific gravity of 1.08, followed by spay drying to obtain 4.0.

Comparative Example 2

1. 100 g thyme was crushed, and passed through a 60-mesh sieve;

2. reflux extraction was performed for 2 h by using 75% ethanol-water solution in a amount of 10 folds by weight of the raw materials;

3. the above extract was filtered through 100-mesh filter cloth to remove the residue, concentrated under reduced pressure (temperature 60° C.-80° C., vacuum degree ≥0.08 Mpa, the same below) to obtain 52 g concentrated solution with a specific gravity of 1.06;

4. recycled ethanol-water solution was adjusted to a concentration of 70%, which was added to the concentrated solution at a volume ratio of 5:1 (ethanol-water solution: concentrated solution); stirred and dissolved at 60° C. for 1.5 h, and refrigerated overnight at 2° C. for 15 h;

5. the refrigerated solution was filtered and the filtrate was concentrated under reduced pressure to obtain 38 g product with a specific gravity of 1.08;

6. the concentrated solution was adsorbed by polyamide resins and eluted with water, 40% ethanol-water solution, 80% ethanol-water solution respectively, wherein the amount of water used is 1BV, the amount of 40% ethanol-water solution used is 2BV, and the amount of 80% ethanol-water solution used is 3BV;

7. a fragment eluted by 80% ethanol-water solution was collected and concentrated under reduced pressure to a specific gravity of 1.06, followed by spay drying to obtain 1.2 g.

Comparative Example 3

1. 100 g *Fructus aurantii* was crushed, and passed through a 60-mesh sieve;

2. reflux extraction was performed for 2 h by using 75% ethanol-water solution in a amount of 10 folds by weight of the raw materials;

3. the above extract was filtered through 100-mesh filter cloth to remove the residue, concentrated under reduced pressure (temperature 60° C.-80° C., vacuum degree ≥0.08 Mpa, the same below) to obtain 70 g concentrated solution with a specific gravity of 1.06;

4. recycled ethanol-water solution was adjusted to a concentration of 70%, added to the concentrated solution at a volume ratio of 5:1 (ethanol-water solution:concentrated solution); stirred and dissolved at 60° C. for 1.5 h, and refrigerated overnight at 2° C. for 15 h;

5. the refrigerated solution was filtered and the filtrate was concentrated under reduced pressure to obtain 58 g product with a specific gravity of 1.08;

6. the concentrated solution was adsorbed by polyamide resins and eluted with water, 40% ethanol-water solution, 80% ethanol-water solution respectively, wherein the amount of water used is 1BV, the amount of 40% ethanol-water solution used is 2BV, and the amount of 80% ethanol-water solution used is 3BV;

7. a fragment eluted by 80% ethanol-water solution was collected and concentrated under reduced pressure to a specific gravity of 1.05, followed by spay drying to obtain 1.8 g.

Experimental Example 1: Bacteriostasis Effect

1. Materials
1.1 Test Bacterial Strain:
*Propionibacterium acnes* (ATCC6919)
1.2 Chinese Medicine Composition Samples:
D1, D2, D3, D4, D5 and D6, stored at 4° C. for use, wherein samples D1 to D6 correspond to the products prepared by Examples 1, 2 and 3, and Comparative examples 1, 2 and 3, respectively.
1.3 Culture Medium:
*Propionibacterium acnes* culture medium (pH was adjusted to 6.6 to 7.0). Agar was added in 15 g per liter to the solid culture medium.

2. Methods
2.1 Preparation of Bacteria Suspension and Inoculation 0.1 ml frozen deposit bacteria suspension was added to 5 ml *Propionibacterium acnes* culture medium and cultured at 37° C. under anaerobic condition for 2 days, thus the bacteria suspension for the experiment was obtained.

2.2 Preparation of Sample Solutions

Samples D1, D2, D3, D4, D5 and D6 were diluted in saline to the test concentration of 0.1%, followed by gradient dilution, respectively. In the first test, the gradient concentrations were 100% (original sample solution), 50%, 25%, 12.5%, 6.25%, 3.125%, 1.56% and 0.78%, respectively. In the second test, the gradient diluted concentrations for second test were 10%, 8%, 6%, 4% and 2%, respectively.

2.3 Preparation of Bacteria Suspension

The bacteria suspension was diluted in *Propionibacterium acnes* culture medium to a final concentration of $10^6$ CFU/ml.

2.4 Culture and Result Judgement

100 μL bacteria suspension and 100 μL sample solution were added to the well. The negative control without adding bacteria and the normal growth control without adding test solution were set at the same time. Each sample was performed in triplicate and the average was taken. Results were observed after anaerobic incubation at 37° C. for 48 h. The presence of turbidity was judged by naked eye and data were read out directly. The prerequisites for result judgement were: the growth control is well, there is no bacteria and the growth is clear for the blank control, and the growth of bacteria in other wells was inhibited with the increasing gradient concentrations of the drugs.

TABLE 1

Results of the first bacteriostasis test in gradient concentrations

| Gradient Concentrations | D1 | D2 | D3 | D4 | D5 | D6 |
|---|---|---|---|---|---|---|
| 50% | − | − | − | − | − | − |
| 25% | − | − | − | − | + | + |
| 12.5% | − | − | − | + | + | + |
| 6.25% | + | + | + | + | + | + |
| 3.125% | + | + | + | + | + | + |
| 1.56% | + | + | + | + | + | + |
| 0.78% | + | + | + | + | + | + |

Note:
+ means presence of bacteria growth;
− means no bacteria growth.

TABLE 2

Results of the second bacteriostasis test by gradient concentrations

| Gradient Concentrations | D1 | D2 | D3 | D4 |
|---|---|---|---|---|
| 10% | − | − | − | + |
| 8% | − | + | − | + |
| 6% | + | + | + | + |
| 4% | + | + | + | + |
| 2% | + | + | + | + |
| 1% | + | + | + | + |

Note:
+ means presence of bacteria growth;
− means no bacteria growth.

2.5 Results

It can be found from the results in Table 1 that the solutions from the three examples with a concentration of 0.1% all had good growth inhibition on *Propionibacterium acnes* when they were diluted to 12.5% or higher concentrations. However, in comparative samples, a desirable effect can be achieved when the concentration of the diluted solutions is 25% or higher for D4 and the concentration is 50% or higher for D5 and D6. It can be found from the results in Table 2, after verification, the bacteriostasis effect can be achieved by D1 and D3 at a concentration of 8%, and by D2 at a concentration of 10%.

It can be known from the above results that minimal addition of the Chinese medicine composition product of the present invention in about 0.01% can achieve basically the inhibition effect on *Propionibacterium acnes*. Also, the Chinese medicine composition of the present invention has a stronger bacteriostasis effect than the medicinal material used solely.

Experimental Example 2: Anti-Inflammation Efficacy Test on Mouse Dermatitis Model 1. Experimental Materials and Methods
1.1 Experimental animals:
Balb/c mice (female, 8-week old, body weight 20 g-25 g) were purchased from Shanghai Slac Laboratory Animal Co. Ltd. (License No. SCXK(Hu)2007-9005).
1.2 Main Experimental Reagents:
2,4-dinitrochlorobenzene (DNCB, analytically pure) was purchased from Shanghai Shunqiang Biotechnology Co. Ltd.; acetone (analytically pure) was purchased from Sinopharm Chemical Reagent Co. Ltd.
2. Chronic Eczematous Dermatitis Mouse Model Induced by DNCB and Drug Therapy On the first day of experiment (d0), all mice were shaved on the back of an area about 2 cm×2 cm. 100 μL of 7% DNCB solution in acetone was taken by pipette and applied to the shaved area of the back of the mice to induce hypersensitivity. From d5, 20 μL of 0.1% DNCB solution was applied to the inner side of the right ear of the mice to challenge and induce chronic dermatitis, once in every three days, total 5 times. To evaluate the anti-dermatitis effects of D1-D6, after the first challenge, different concentrations of diluted solution or solvent of D1-D6 were applied to the sensitized area of the right ear and the back of the mice, twice per day. Skin lesions of the sensitized area of the back of the mice in the dermatitis model group and drug treatment group were observed 48 h after each challenge. All mice were sacrificed 48 h after the last challenge. Left and right auricle pieces (diameter about 8 mm) were removed by a puncher and their mass were measured on an analytical balance. The mass difference between the two auricles, which reflects the degree of ear swelling, was calculated.

3. Experimental Results
3.1 Primary Evaluation Results of Anti-Dermatitis Effect of D1-D6

Mice were divided into 5 groups at random and each group has 4 mice used in the evaluation experiment for each component. These 5 groups are: normal control group, solvent control group, 5%, 10% and 15% D1-D6 diluted solution treatment groups, respectively. For the normal control group, only acetone was applied to the hair-removed-area on the back and right ear. For the solvent control group, DNCB solution in acetone was applied to induce dermatitis on the hair-removed-area on the back and right ear, and after the first challenge the solvents for the test component (0.1% solution in water for D1-D6) were applied. For the 5%, 10% and 15% D1-D6 diluted solution treatment groups, DNCB solution in acetone was applied to the hair-removed-area on the back and right ear to induce dermatitis, followed by application of test components after first challenge, wherein the concentrations thereof are 5%, 10% and 15%, respectively. Skin lesions of the sensitized area of the back of the mice in all experimental groups were observed 48 h after each challenge, and photos were taken. The results indicated that components D5 and D6 basically failed to show the pharmacological effect of relieving dermatitis in the dose range of 5%-15%, while components D1 to D4 have certain pharmacological effect of relieving dermatitis at the dose of 15%. The results are shown in Table 3.

TABLE 3

Data of D1-D6 diluted solution for mouse ear swelling model

| No. | Blank group Average of difference between left and right auricle weight(g) | Model group Average of difference between left and right auricle weight(g) | Solvent group Average of difference between left and right auricle weight(g) | 5% treatment group Average of difference between left and right auricle weight(g) | 10% treatment group Average of difference between left and right auricle weight(g) | 15% treatment group Average of difference between left and right auricle weight(g) |
|---|---|---|---|---|---|---|
| D1 | 0.4 | 3.9 | 4.9 | 3.1 | 2.6 | 1.4 |
| D2 | 0.8 | 3.7 | 4.1 | 3.3 | 2.2 | 0.8 |
| D3 | 0.7 | 2.8 | 3.2 | 3.4 | 2.3 | 0.4 |
| D4 | 1.0 | 4.1 | 3.3 | 3.8 | 3.0 | 2.0 |
| Maximum | 1.0 | 4.1 | 4.9 | 3.8 | 3.0 | 2.0 |
| Minimum | 0.4 | 2.8 | 3.2 | 3.1 | 2.2 | 0.4 |
| Average | 0.725 | 3.625 | 3.875 | 3.4 | 2.525 | 1.15 |

It can be known from the data in Table 3, 0.1% solutions of D1-D4 all have an inflammation-relieving effect at different concentrations, but the effect was not remarkable at the concentration 5%, slightly improved at the concentration 10% and remarkable at the concentration 15%. In vertical comparison, D1, D2 and D3 have similar effect overall and are slightly better than D4. While D5 and D6 had not received remarkable relief of the inflammation on the back, thus no comparison was made.

It can be found from the results of bacteriostasis test, the minimum application concentration of D3 can be as low as 8% while the minimum concentration of D4 is higher than 12.5%. It can be found from the ear swelling data in mouse inflammation model, D3 and D4 solutions have similar effect on inflammation relieving at the concentration 5%, while at the concentrations 10% and 15%, the data of D3 is much smaller than that of D4 with a difference of higher than 20%, showing D3 has a much better anti-inflammation effect than D4 at the same concentration. These results indicated that mangosteen pericarp, thyme and Fructus aurantii have a synergic effect on bacteriostasis and inflammation relieving.

Experimental Example 3: Clinical Experiment 0.1% of the acne-removing Chinese medicine composition in example 1 of the present invention was added to general basal cream and applied to lesions of the subjects. Apparent redness and swellings were relieved in 0.5 h-1 h; no uncomfortable feelings from acne, such as swelling and pricking pain, in 4 h-6 h; and all the wounds scabbed within 24 h. After a long term application, those subjects who suffered from acne for a long time, had a significantly decreased distribution density of acne on their faces, and the inflammations were more slight than normal population when acne occurred. The acne-removing Chinese medicine compositions of example 2 and example 3 have comparable effect as example 1 in clinic.

The invention claimed is:

1. An acne-removing Chinese medicine composition which is prepared from the following raw materials by weight parts:

| | |
|---|---|
| mangosteen pericarp | 60 to 80 parts |
| thyme | 10 to 20 parts |
| *fructus aurantii* | 10 to 20 parts. |

2. A method for preparing an acne-removing Chinese medicine composition, comprising the steps of: mixing 60 to 80 parts by weight of mangosteen pericarp, 10 to 20 parts by weight of thyme and 10 to 20 parts by weight of *fructus aurantii*; extracting with ethanol; collecting and purifying the extraction solution.

3. The preparation method of claim 2, wherein ethanol extraction is performed by using 8 to 12 folds by weight of 76%-95% ethanol-water solution for heating reflux extraction for 1 h-2.5 h.

4. The preparation method of claim 2, wherein the purification specifically comprises the following steps:
   a. extraction solution is concentrated after filtration, dissolved in ethanol-water solution and refrigerated overnight; and
   b. filtration is performed, and the filtrate is adsorbed by macroporous adsorption resin and eluted by elution solution.

5. The preparation method of claim 4, wherein in step a the concentration is conducted to a specific gravity of 1.05 to 1.1.

6. The preparation method of claim 4, wherein in step a the volume ratio of ethanol in the ethanol-water solution is 70%-80%.

7. The preparation method of claim 4, wherein in step a the refrigeration overnight is performed at 0° C. to 4° C. for 12 h-18 h.

8. The preparation method of claim 4, wherein in step b the elution is performed by water, 20%-40% ethanol-water solution, 60%-80% ethanol-water solution, successively, and the fragment eluted by 60%-80% ethanol-water solution is collected.

9. A Chinese medicine composition prepared by the preparation method of claim 2.

10. An acne-removing preparation, characterized in that it is prepared from the Chinese medicine composition of claim 1 and acceptable excipients.

* * * * *